United States Patent [19]

Gray et al.

[11] Patent Number: 4,593,687
[45] Date of Patent: Jun. 10, 1986

[54] ENDOTRACHEAL CATHETER

[76] Inventors: Leo C. Gray, Caroga, N.Y.; Martin D. Gray, executor, R.D. 1, Box 1312, Fort Ann, N.Y. 12827

[21] Appl. No.: 546,943

[22] Filed: Oct. 31, 1983

[51] Int. Cl.$^4$ ............................................. A61M 16/00
[52] U.S. Cl. ........................... 128/200.26; 128/207.14; 604/104; 604/164; 604/281; 604/283
[58] Field of Search ...................... 128/207.14, 207.15, 128/200.26, 657, 343, 345; 604/104, 164, 278, 280, 281, 282, 283, 105, 106

[56] References Cited

U.S. PATENT DOCUMENTS

| | | | |
|---|---|---|---|
| 3,426,744 | 2/1969 | Ball | 604/282 |
| 3,674,014 | 7/1972 | Tillander | 128/657 |
| 3,734,083 | 5/1973 | Kolin | 604/104 |
| 3,946,741 | 3/1976 | Adair | 604/105 |
| 4,154,242 | 5/1979 | Termanini | 604/105 |
| 4,244,362 | 1/1981 | Anderson | 128/200.26 |
| 4,282,876 | 8/1981 | Flynn | 604/280 |
| 4,300,550 | 11/1981 | Gandi et al. | 128/207.18 |
| 4,315,513 | 2/1982 | Nawash et al. | 604/283 |
| 4,431,005 | 2/1984 | McCormick | 128/207.14 |

FOREIGN PATENT DOCUMENTS 3015593 10/1981 Fed. Rep. of Germany ........................ 128/207.15

OTHER PUBLICATIONS

Roven et al., "A Directional Catheter", Lancet, Oct. 1964, pp. 793-794.

Primary Examiner—Henry J. Recla
Assistant Examiner—Karin M. Reichle
Attorney, Agent, or Firm—Roland H. Shubert

[57] ABSTRACT

A method and apparatus for introducing oxygen or a saline solution directly into the trachea in order to facilitate respiration. The apparatus includes a sharp pointed magnetic stylet, a similarly shaped rounded end magnetic probe, and a radiopaque flexible bulbed end plastic catheter tube with three equally spaced axially embedded memory wires.

The small diameter catheter tube and the incorporated magnetic stylet is inserted through the wall of the throat and thorugh the flesh and wall of the trachea between the second and third tracheal rings.

The retraction and removal of the magnetic stylet causes the expansion of the catheter and locks the tube end inside the tracheal wall. The catheter tube is the vessel for the conveyance of oxygen or a saline solution into the trachea. Insertion of the magnetic probe into the catheter tube causes the contraction of the catheter tube end and allows same to be removed and reinserted as necessary.

4 Claims, 6 Drawing Figures

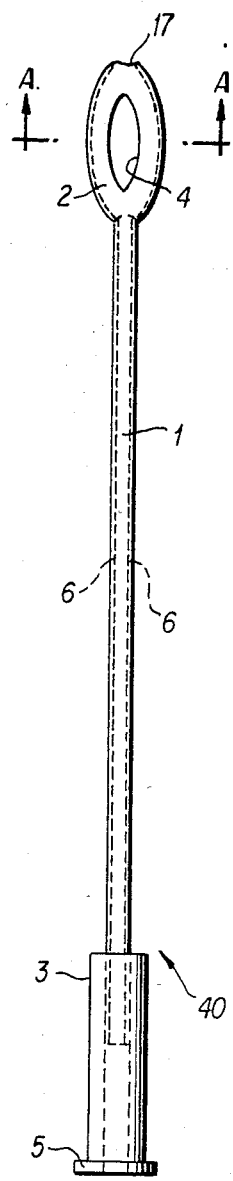
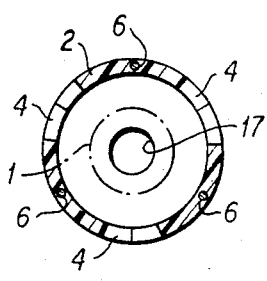
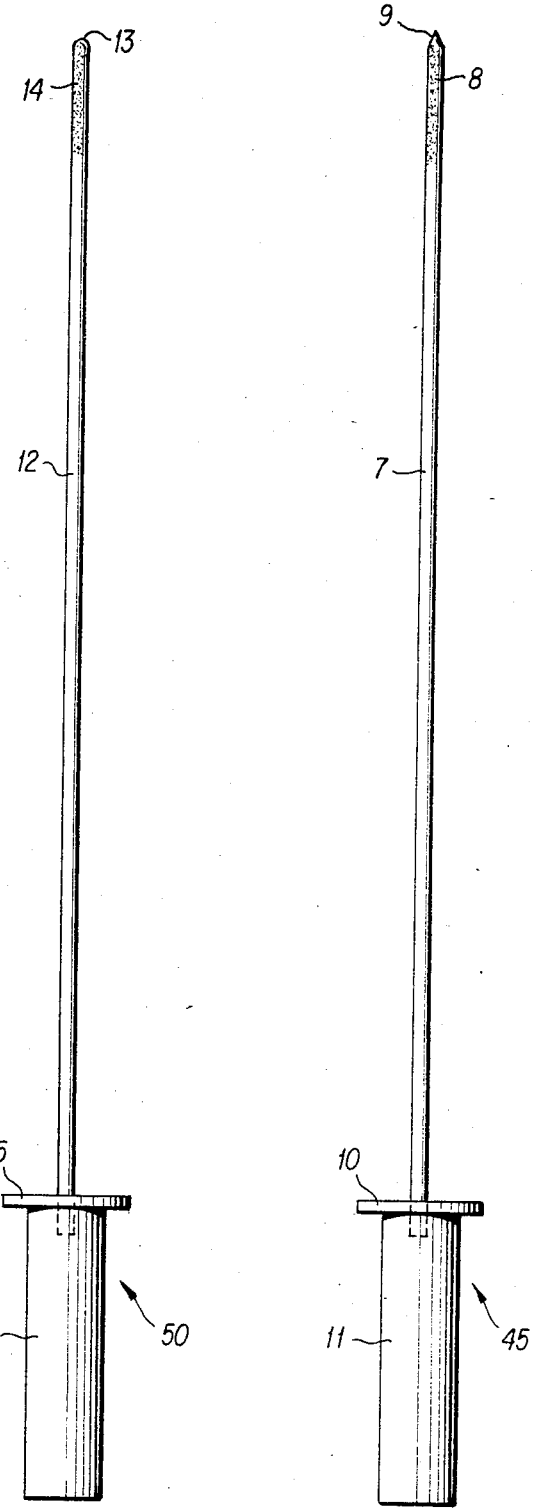
FIG. 1
FIG. 2
FIG. 3
FIG. 4

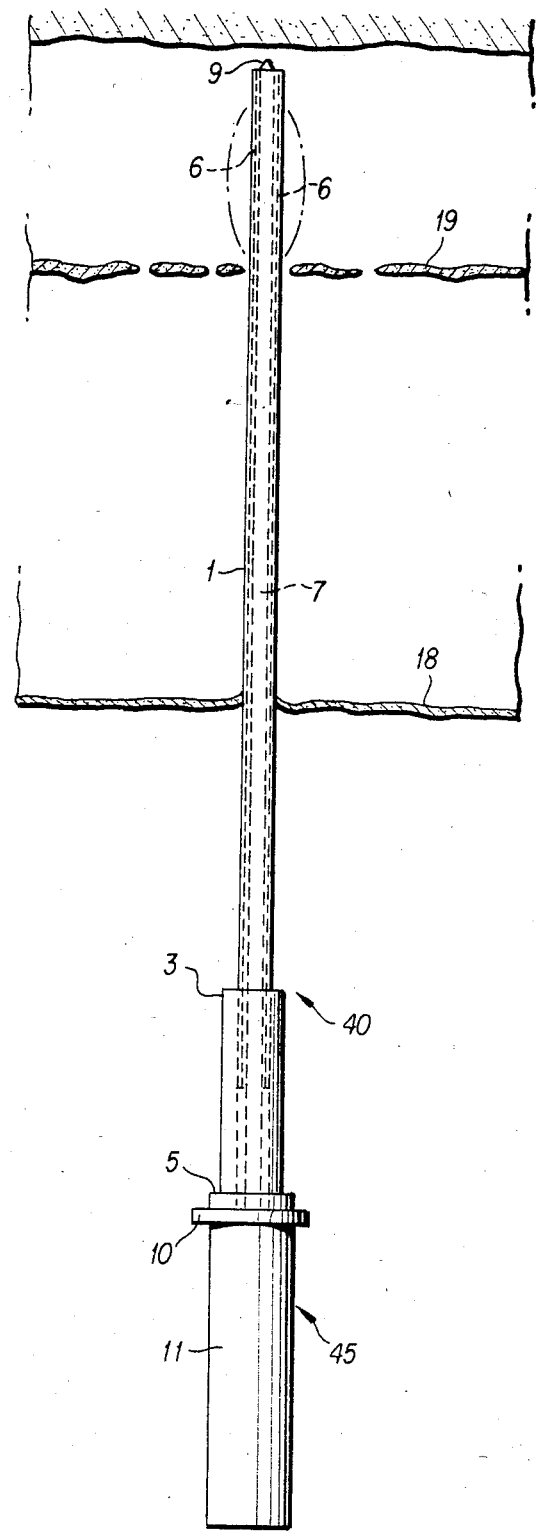
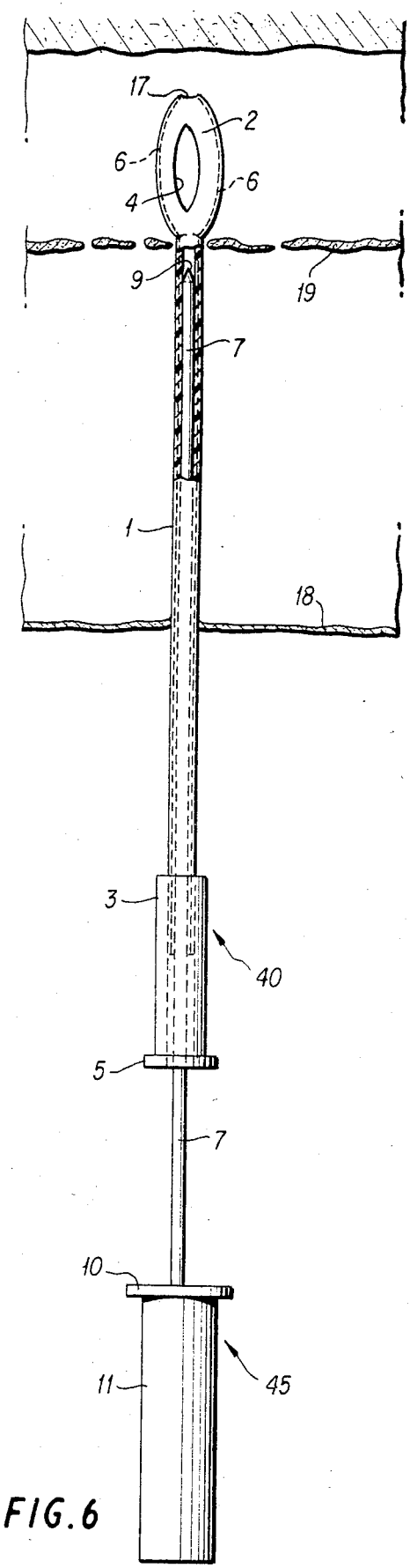
FIG. 5
FIG. 6

ENDOTRACHEAL CATHETER

SUMMARY OF THE INVENTION

The endotracheal catheter consists of three items; the catheter, the magnetic stylet and the magnetic probe.

The catheter is a piece of flexible tubing approximately 1.7 millimeters in diameter and approximately 7.5 centimeters in length with three axially imbedded deformed memory wires. The external end is equipped with a Leur Lock adapter. The inner elliptically shaped end has three slits approximately 0.64 centimeters in length situated midway between the deformed memory wires.

The magnetic stylet will be of a lesser diameter, for a sliding fit, than the internal diameter of the catheter and shall have a pointed end to be used to insert the catheter into the trachea.

The magnetic probe is to be used for retraction and re-insertion of the catheter and is similar to the magnetic stylet except that the inner end is rounded.

The endotracheal catheter in itself serves two purposes; the first is the transportation of oxygen directly to the trachea or windpipe, whereby the natural respiratory system can move it with ease to the bronchi and lungs without waste and without as much exertion as is required by normal inhalation.

The second purpose of the endotracheal catheter is to allow injection of a saline liquid wash solution into the trachea which assists in loosening the secretions in the trachea and larnyx, and stimulates coughing which immediately causes expectoration of the sputum, the result being the freer passage of air during the normal respiratory process.

In order to utilize the endotracheal catheter, a surgical procedure must be performed to introduce the catheter into the trachea. After anesthetization of the area between the second and third tracheal rings, the magnetic stylet is inserted into the catheter so that the deformed memory wires are attracted to the stylet making the external diameter of the catheter the same for the full length.

Using the combination catheter and magnetic stylet as the piercing tool, the instrument is forced through the wall of the throat, extending approximately 1.25 centimeters into the trachea cavity. The magnetic stylet is then withdrawn, allowing the memory wires in the catheter to expand and thereby retain the internal end of the catheter in the trachea. At this point, oxygen is introduced through the catheter.

At such time as it becomes necessary to perform a liquid wash, the oxygen supply must first be disconnected from the catheter. A syringe with approximately 1½ cubic centimeters of saline solution would then be forcibly injected through the Leur Lock adapter of the catheter causing instantaneous expectoration of the sputum. After removal of the syringe, the oxygen supply would be reconnected to the Leur Lock adapter.

The magnetic probe is used to remove and re-install the catheter through the existing stoma for the purpose of cleaning or changing the catheter. The magnetic probe would be utilized in the same manner as the magnetic stylet to attract the memory wires.

The endotracheal catheter eliminates the need for nasal cannulas and masks for oxygen inhalation. The latter devices deliver oxygen to the anatomic dead space of the trachea, the larynx, and the nasopharynx, and the atmosphere. Only a small percentage of the oxygen administered in this manner reaches the alveoli. This device, the endotracheal catheter, eliminates this waste.

Cannulas cause drying and irritation of the upper airway. Masks are hot and confining. Cannulas and masks are difficult to keep in place. Eating and speaking are also compromised by these archaic methods; the endotracheal catheter eliminates these inconveniences.

This invention does not inhibit the user from being able to talk as does a normal tracheostomy tube or a trach-button because of the minute diameter.

Using the entrotracheal catheter, no humidification is necessary as the oxygen enters the already humidified area of the trachea.

This invention has many far-reaching possibilities. It will enhance the physical well-being of people suffering from all types of respiratory diseases including emphysema, bronchitis, black lung, asthma, those people suffering from pollen-inhibited allergies, and even those suffering from the common cold.

BRIEF DESCRIPTION OF THE DRAWINGS

FIG. 1 is an enlarged side elevation view of the catheter tube.

FIG. 2 is an enlarged sectional view taken along line A—A of FIG. 1.

FIG. 3 is an enlarged side elevation view of the magnetic probe.

FIG. 4 is an enlarged side elevation view of the magnetic stylet.

FIG. 5 is an enlarged side elevation view of the combined and assembled apparatus shown in FIG. 1 and FIG. 4 inserted through the trachea wall.

FIG. 6 is an enlarged side elevation view of the combined apparatus shown in FIG. 1 and FIG. 4 inserted through the trachea wall with the apparatus shown in FIG. 4 partially retracted.

BACKGROUND OF INVENTION

1. Field of Invention

The invention relates to a plastic tube which can be inserted through the flesh and the wall of the trachea allowing oxygen to be introduced to the lungs or a saline solution introduced to the trachea. This invention relates to medical devices and methods, and more particularly to a device and method for introducing oxygen or a saline solution into the trachea.

In addition, methods of the prior art tend to be cumbersome and expensive. Accordingly, the need exists for a portable device which would supply the necessary catalysts to the lungs without creating physical abuse in order to facilitate respiration and removal of secretions from the bronchi and lungs.

With that need in mind, it is therefore the general object of this invention to provide a method and apparatus for introduction of oxygen into the lungs in order to decrease the muscular efforts for normal respiration and secondly to introduce liquid wash solution into the trachea to assist in breakdown of secretions and stimulate coughing to cause expectoration of the sputum and thereby result in the less obstructed passage of air during the normal respiratory process.

It is the further object of this invention to provide the apparatus which will remain in place in the trachea and can be therefore in operation while the user is walking, eating, sleeping or performing normal daily functions.

The objectives of this invention are achieved by providing a piece of flexible tubing with an inside diameter of approximately 1.7 millimeters and a length of approximately 7.5 centimeters in working length, a pointed rigid stainless steel cylinder and a rounded end stainless steel cylinder.

2. Description of the Prior Art

Heretofore, the following methods and procedures were commonly employed to facilitate breathing, loosening and expectoration of secretions, and humidification of oxygen;

1. Lying in an elevated bed which tended to keep the secretions in the lungs.
2. Postural drainage which is the art of pounding the anatomy from all sides to assist in loosening the secretions in the bronchi and lungs.
3. Ultrasonic nebulization, the inhalation of fine particles of water to assist in loosening the secretions in the respiratory tract.
4. Forced coughing to expectorate the secretions.
5. Humidification of oxygen to prevent drying of the anatomical area to the trachea.
6. Inhalation of oxygen by way of nasal canula or face masks.

Utilizing the endotracheal catheter, the above procedures, often detrimental and wasteful, are no longer required.

DETAILED DESCRIPTION OF THE DRAWINGS

Referring now to the various figures of the drawing wherein like reference characters refer to like parts, there is shown in FIG. 1 a catheter 40 shown by itself.

Catheter 40 comprises a small, flexible, preferably radiopaque tube 1 which, by way of illustration, may be approximately 1.7 millimeter in internal diameter and approximately 7.5 centimeters in length. One end of tube 1, that end which is inserted into the trachea, terminates in an aperture 17 which is smaller in diameter than is the inside diameter of tube 1. The other, or external, end of tube 1 terminates in means 3 for detachable connection to another conduit. Means 3 may comprise a Leur Lock adapter.

Axially embedded in an equi-spaced relationship within the walls of tube 1 are a plurality, preferably three, of magnetic steel memory wires 6 which, if unrestrained, exert an outwardly bowing force on the wall of tube 1 relative to its axis. That end of tube 1 adjacent aperture 17 is provided with a plurality of cuts extending axially through the wall of tube 1, one cut spaced between each embedded magnetic wire. Outwardly bowing forces imposed on the tube wall by the embedded wires spreads each of the cuts into an elliptically shaped slot 4, as shown in FIGS. 1 and 2, to form a bulbous, elliptically shaped lock or anchor 2. However, under the influence of a magnetic field within the interior of tube 1, wires 6 assume a straight and parallel attitude. Such a magnetic field may be imposed by insertion of a probe, such as is shown in FIG. 3 or a stylet of the type illustrated in FIG. 4, through the interior of the tube until the magnetized end of either the probe or stylet is positioned adjacent slots 4. Withdrawal of the probe or stylet removes the magnetic field allowing the end of tube 1 to expand to a bulbous shape which acts to lock or anchor the catheter end within the trachea as is best shown in FIG. 6.

The unflared end of flexible tube 1 is securely embedded in Leur Lock adapter 3, a hollow rigid plastic cylinder with a flanged end 5. The purposes and usage of catheter 40 are to be described later. The diameter of stylet 45 is slightly smaller than the inside diameter of tube 1 but is greater than the diameter of aperture 17 thus allowing the pointed and magnetized end 9 of the stylet to protrude through aperture 17.

Magnetic stylet 45 comprises a rigid stainless steel cylinder 7 which is sharp and pointed at one end 8, the same end being magnetized 9 and the other end being securely embedded into the arresting flange 10 and finger grip 11, the purposes and usage of which will be described later.

Magnetic probe 50 comprises a rigid stainless steel cylinder 12 which is rounded at one end 13, the same end being magnetized and the other end being securely embedded into the arresting flange 15 and finger grip 16.

The usage of the endotracheal catheter components 40, 45 and 50 is accomplished in five step sequences. The first sequence entails the following steps.

The magnetic stylet 45 is inserted by hand gripping the finger grip 11 and inserting the cylinder 8 through the Leur Lock adapter 3 of the catheter 40 and through the radiopaque tube 1.

As the stylet magnet 8 passes through the elliptically shaped lock 2, the axially embedded spring steel wires 6 become attracted to the stylet magnet 8 and cause the elliptically shaped lock 2 to contract and form the shape of the radiopaque tube 1. The united catheter 40 and magnetic stylet 45 are completely assembled for use when the Leur Lock adapter flange abuts the magnetic stylet arresting flange 10.

The second sequence entails the insertion of the pointed end 9 of the united catheter 40 and magnetic stylet 45 assembly through the wall of the throat 18, FIG. 5 and approximately 1.5 centimeters beyond the inside surface of the tracheal wall 19.

The third sequence entails the removal of the magnetic stylet 45 from the catheter assembly 40. While the fingers of one hand hold the Leur Lock adapter 3 of the catheter 40, in a steady position, the fingers of the other hand grip the finger grip 11 of the magnetic stylet 45 and as in FIG. 6 retract the cylinder 7 from the radiopaque tube 1.

As the cylinder 7 retracts through the radiopaque tube 1, the penetrated end of same tube 1 expands FIG. 6 to lock the catheter radiopaque tube end 2 inside the tracheal wall 19.

The fourth sequence entails actual usages of the invention. The first usage of the catheter assembly 40 in place is to secure a controlled oxygen supply to the leur lock adapter 3. As oxygen flows through the radio paque tube 1 its flow is dispersed through the restricted circular aperture 17 at the discharge end of the elliptically shaped lock 2 as well as the three elliptical slots, along the axis of same lock 2. At such time that it becomes necessary to perform the liquid wash, the oxygen supply must be disconnected from the Leur Lock adapter 3. With the elliptically shaped lock 2 still in place, a syringe with approximately 1½ cubic centimeters of saline solution is forcibly injected through the Leur Lock adapter 3 and through the restricted circular aperture 17 at the discharge end of the elliptically shaped lock 2 as well as the three elliptical slots along the axis of the same lock 2.

The fifth and final sequence entails the uses of the magnetic probe 50 in withdrawing or reinserting the radiopaque tube 1. The withdrawing of the radiopaque tube 1 is effected by holding the Leur lock adapter 3 steady with the fingers of one hand, holding the finger grip 16 of the magnetic probe 50 in the other hand and inserting the cylinder 12 of the magnetic probe 50 through the Leur Lock adapter 3 of the catheter 40 and through the radiopaque tube 1. As the probe magnet 14 passes through the elliptically shaped lock 2, the axially embedded spring steel wires 6 become attracted to the probe magnet 14 and cause the elliptically shaped lock 2 to contract and form the shape of the radiopaque tube 1. The united cathether 40 and magnetic probe 50 are completely assembled for use when the Leur Lock adapter flange 5 abutts the magnetic probe arresting flange 15. The united assembly 40 and 50 can be withdrawn through the trachea wall 19 and wall of the throat 18 by gripping the Leur Lock adapter 3 with the hand and effecting withdrawal.

CLAIMS

Without further elaboration, the forgoing will so fully illustrate our invention that others may, by applying current or future knowledge readily adapt the same for use under varying conditions of service.

What is claimed of the invention is:

1. An endotracheal catheter comprising a relatively small diameter flexible tubing member for placement through the tracheal wall of a human; one end of said tubing member adapted to form an elliptically shaped bulbous expandable anchoring lock with the trachea after insertion therein, and the other end of said tubing member having means adapted for connection to a conduit; the one end of said tubing member adapted to form said expandable anchoring lock comprising a plurality of equi-spaced magnetic wires embedded longitudinally within the wall area of said one end of said tubing member and a corresponding number of longitudinal cuts extending through the wall of said tubing member and positioned midway between each of said magnetic wires; said magnetic wires being bowed outwardly and adapted to flex to straight and parallel positions with respect to each other under the influence of a magnetic field created within the interior of said tubing member and to bow outwardly upon removal of said magnetic field whereby said elliptically shaped bulbous anchoring lock is formed within the trachea by the spreading of said flexible tubing member about said wires and wherein said cuts form elliptically shaped apertures through which a fluid can flow.

2. The endotrachael catheter of claim 1 wherein said tubing member is constructed of a radiopaque material.

3. The endotracheal catheter of claim 1 wherein said means adapted for connection to a conduit comprises a Leur Lock adapter.

4. The endotracheal catheter of claim 1 wherein the one end of said tubing member adjacent said anchoring lock terminates in an aperture having a diameter smaller than the inside diameter of said tubing member.

* * * * *